United States Patent
Brandvold et al.

(10) Patent No.: US 7,038,090 B1
(45) Date of Patent: May 2, 2006

(54) PROCESS AND CATALYST FOR PRODUCING HYDROPEROXIDES

(75) Inventors: Timothy A. Brandvold, Arlington Heights, IL (US); Gregory J. Lewis, Mount Prospect, IL (US); Lisa M. King, Crystal Lake, IL (US); Lawrence E. Brewer, Lockport, IL (US)

(73) Assignee: UOP LLC, Des Plaines, IL (US)

( * ) Notice: Subject to any disclaimer, the term of this patent is extended or adjusted under 35 U.S.C. 154(b) by 83 days.

(21) Appl. No.: 10/816,128

(22) Filed: Apr. 1, 2004

(51) Int. Cl.
*C07C 409/00* (2006.01)
(52) U.S. Cl. .................. 568/575; 568/574; 568/569; 568/571; 568/573; 549/529; 549/530
(58) Field of Classification Search .............. 568/575, 568/574, 569, 571, 573; 549/529, 530
See application file for complete search history.

(56) References Cited

U.S. PATENT DOCUMENTS

| 4,201,875 | A | * | 5/1980 | Wu et al. ................. 568/575 |
| 4,202,992 | A | * | 5/1980 | Coltrin et al. ............ 568/575 |
| 4,262,143 | A | * | 4/1981 | Becker .................... 549/529 |
| 4,293,720 | A | * | 10/1981 | Iwaki et al. ............. 568/575 |
| 5,504,256 | A | * | 4/1996 | Bond et al. .............. 568/575 |
| 6,476,276 | B1 | * | 11/2002 | Matsui et al. ........... 568/569 |
| 6,700,005 | B1 | * | 3/2004 | Kremers et al. .......... 549/529 |

* cited by examiner

*Primary Examiner*—Johann Richter
*Assistant Examiner*—Chukwuma Nwaonicha
(74) *Attorney, Agent, or Firm*—John G. Tolomei; James C. Paschall; John G. Cutts, Jr.

(57) ABSTRACT

A process and catalyst for preparing organic hydroperoxides by oxidizing hydrocarbon compounds in the presence of an oxygen-containing gas and a catalyst containing a transition metal on a solid support.

12 Claims, No Drawings

PROCESS AND CATALYST FOR PRODUCING HYDROPEROXIDES

FIELD OF THE INVENTION

The present invention relates to a process for preparing organic hydroperoxides by oxidizing hydrocarbon compounds in the presence of an oxygen-containing gas and a catalyst containing a transition metal oxide component.

BACKGROUND OF THE INVENTION

It is known that compounds possessing a carbon-hydrogen bond can be oxidized with molecular oxygen to products containing a hydroperoxide group where the original carbon-hydrogen bond was located. The resulting hydroperoxide is useful in the conversion of sulfur containing hydrocarbons to sulfur oxidized compounds which may then be more easily removed from a hydrocarbon stream containing sulfur compounds. Depending upon the particular starting compound, hydroperoxides can be produced with rather high selectivity under suitable oxidation conditions. At the same time, it is recognized that in order to achieve a reasonable degree of selectivity to the desired hydroperoxide, relatively mild conditions need to be utilized because under more severe conditions oxidation of the starting compound can proceed in a non-selective manner and can oxidize the starting compound to such products as carbon dioxide and water under extreme conditions. Under the relatively mild conditions needed for the selective oxidation of the starting compounds to hydroperoxides, a penalty is then exacted from the process in terms of the relatively slow reaction rate for the oxidation reaction. Hence, it is desirable to provide a relatively selective oxidation reaction for the production of hydroperoxides while at the same time attaining a faster rate of oxidation under the relatively mild conditions utilized.

Information Disclosure

U.S. Pat. No. 5,504,256 (Bond et al.) discloses a method for preparing hydroperoxides by oxidizing aryl alkyl hydrocarbons having a benzylic hydrogen with an oxygen containing gas using as a catalyst an oxo (hydroxo) bridged tetranuclear metal complex having a mixed metal core, one metal of the core being a divalent metal selected from Zn, Cu, Fe, Co, Ni, Mn or mixtures thereof and another metal being a trivalent metal selected form In, Fe, Mn, Ga and Al.

U.S. Pat. No. 4,201,875 (Wu et al.) discloses the preparation of organic hydroperoxides by reacting an organic compound with oxygen in the presence of a catalyst comprising metallic silver supported upon an inorganic support selected from the oxides and carbonates of metals of Groups IIA, IIB, IIIB and IVB.

SUMMARY OF THE INVENTION

The present invention provides a process for preparing organic hydroperoxides. Hydroperoxides are produced by reacting an organic compound with oxygen in the presence of a solid catalyst. The present invention is broadly applicable to the oxidation of any organic compound containing at least one carbon-hydrogen bond capable of being oxidized to a hydroperoxide-carbon bond. A preferred organic compound is an aryl alkyl hydrocarbon having a benzylic hydrogen. Preferred catalysts are described hereinafter.

Other embodiments of the present invention encompass further details such as feedstocks, catalyst preparations, catalyst compositions and operating conditions, all of which are hereinafter disclosed in the following discussion of each of these facets of the invention.

DETAILED DESCRIPTION OF THE INVENTION

In accordance with the present invention hydroperoxides are produced by reacting an organic compound with oxygen in the presence of a catalyst comprising at least one transition metal component. This catalyst can take on many forms. One embodiment of the catalyst includes simple transition metal oxides (a simple transition metal oxide contains one transition metal in the phase, such as MnO or $Mn_3O_4$) of empirical formulation in the anhydrous state $$(M1)_a^{m+}H_dO_z$$

where M1 is a transition metal selected from the set Mn, Co, Cr, V, Mo, Fe, Cu, and Ni, which comprises between 0.1% and 90% of the catalyst by weight, "a" is the moles of the M1 metal in the transition metal oxide and is defined to be equal to 1, "m" is the average valence of M1 and is greater than 0, "d" is the mole ratio of hydrogen to M1 and varies from 0 to about "z", and "z" is the mole ratio of O to M1 and is given by $$z=(a\cdot m+d)/2=(m+d)/2$$

Another embodiment includes physical mixtures of simple transition metal oxides, the mixture given by the empirical formulation in the anhydrous state $$(M1)_a^{m+}H_dO_z$$

where M1 includes at least two metals selected from the group Mn, Co, Cr, V, Mo, Fe, Cu, and Ni, which together comprise between 0.1% and 90% of the catalyst by weight, "a" is the sum of the mole fractions of the individual M1 metals and is defined to be 1, "m" is the weighted average valence of the M1 metals and is greater than 0, "d" is the mole ratio of hydrogen to the moles of M1 metals and varies from 0 to about "z", and z is the mole ratio of oxygen to the M1 metals and is given by $$z=(a\cdot m+d)/2$$

Any combination of these simple transition metal oxides can be mixed in any proportion to obtain the desired catalyst provided the weight fraction of M1 falls in the 0.1% to 90% range.

Another embodiment of the catalyst includes a complex transition metal oxide (a complex transition metal oxide contains one transition metal along with either another transition metal, any other metal, or any main group element in the same phase, e.g., $MnMoO_4$, $MnPO_4$, $Li_2MnO_3$) consisting of at least one transition metal oxide component. Such oxides in the anhydrous state are described by the empirical formulation $$(M1)_a^{m+}(M2)_b^{n+}(M3)_c^{p+H}{}_dO_z$$

where M1 is a transition metal component selected from Mn, Co, Cr, V, Mo, Fe, Cu, Ni, and mixtures thereof which comprise between 0.1% and 90% of the catalyst by weight, "a" is the sum of the mole fractions of M1 metals and is defined to be 1, "m" is the weighted average valence of the M1 metals and is greater than 0, M2 is selected from the group of cations and metals including ammonium ion, organoammonium ions, alkali metals, alkaline earth metals, rare earth metals, selected early transition metals, and main group metals, including $NH_4^+$, n-propylammonium, Li, Na, K, Rb, Cs, Mg, Ca, Sr, Ba, La, Ce, Sm, Pr, Yb, Sc, Y, Ti, Zr, Hf, Al, Ga, In, Sn, Bi, and mixtures thereof, "b" is the mole ratio of M2 cations and metals to the M1 metals and is greater than or equal to 0, "n" is the weighted average valence of the M2 cations and metals and is greater than 0, M3 is selected from the main group elements that form complex oxoanions such as C, Si, P, and Ge, "c" is the mole ratio of M3 to the M1 metals and is greater than or equal to 0, "p" is the weighted average valence of M3 and is greater than 0, "d" is mole ratio of hydrogen to the M1 metals and varies from 0 to about "z", "z" is mole ratio of O to M1 metals and is given by $$z(a \cdot m + b \cdot n + c \cdot p + d)/2$$

If b+c=0, then the complex oxide consists of more than one M1 transition metal. When there is more than one M1 metal, e.g., M1(1), M1(2), M1(3) . . . , "a", the number of moles of the M1 metals in the complex oxide is defined to be 1 and is given by the sum of mole fractions, $a_{M1}(1)$, of the individual M1 metals:

$$a = a_{M1(1)} + a_{M1(2)} + a_{M1(3)} + \ldots = 1$$

where the individual mole fractions $a_{M1(1)}$, etc. are given by $$a_{M1(1)} = \text{moles M1(1)/total moles M1}$$

Likewise, when M1 is more than one metal, "m", the weighted average valence of M1, is given in terms of the individual mole fractions of each M1 metal, $a_{M1(n)}$, and the individual average valence of each M1 metal, $m_{M1(n)}$, by the formulation $$m = \frac{(a_{M1(1)} \cdot m_{M1(1)} + a_{M1(2)} \cdot m_{M1(2)} + a_{M1(3)} \cdot m_{M1(3)} + \ldots)}{(a_{M1(1)} + a_{M1(2)} + a_{M1(3)} + \ldots)}.$$

For multiple M2 and M3 species, the mole ratios "b" and "c" are defined in terms of the moles of the individual M2 and M3 species and the M1 metals by:

$b$=sum moles M2 species/sum moles M1 metals $c$=sum moles M3 species/sum moles M1 metals $$b = b_{M2(1)} + b_{M2(2)} + b_{M2(3)} + \ldots$$

$$c = c_{M3(1)} + c_{M3(2)} + c_{M3(3)} + \ldots$$

where the individual $b_{M2(1)}$, $c_{M3(1)}$, etc., are given by the ratios $$b_{M2(1)} = \text{moles M2(1)/sum moles M1 metals}$$

$$c_{M3(1)} = \text{moles M3(1)/sum moles M1 metals}.$$

The weighted average valences for M2 and M3, "n" and "p", are given in terms of the mole ratios for the individual M2 and M3 species, $b_{M2(1)}$, $c_{M3(1)}$, etc., and their associated valences, $n_{M2(1)}$, $p_{M3(1)}$, etc., by $$n = \frac{(b_{M2(1)} \cdot n_{M2(1)} + b_{M2(2)} \cdot n_{M2(2)} + b_{M2(3)} \cdot n_{M2(3)} + \ldots)}{(b_{M2(1)} + b_{M2(2)} + b_{M2(3)} + \ldots)}$$

$$p = \frac{(c_{M3(1)} \cdot p_{M3(1)} + c_{M3(2)} \cdot p_{M3(2)} + c_{M3(3)} \cdot p_{M3(3)} + \ldots)}{(c_{M3(1)} + c_{M3(2)} + c_{M3(3)} + \ldots)}.$$

Another embodiment of the catalyst includes employing physical mixtures of the complex oxides, physical mixtures of simple oxides or physical mixtures of complex oxides and simple oxides where the simple and complex oxides are compounds of M1, M2, and M3 in which at least one of the oxide components in the mixture contains at least one M1 metal, the mixture given by the empirical formulation when in an anhydrous state $$(M1)_a^{m+}(M2)_b^{n+}(M3)_c^{p+}H_d^{\phantom{d}}O_z$$

where M1 is a transition metal component selected from Mn, Co, Cr, V, Mo, Fe, Cu, Ni, and mixtures thereof which comprise between 0.1% and 90% of the catalyst by weight, "a" is the sum of the mole fractions of M1 metals and is defined to be 1, "m" is the weighted average valence of the M1 metals and is greater than 0, M2 is selected from the group of cations and metals including ammonium ion, organoammonium alkali metals, alkaline earth metals, rare earth metals, selected early transition metals, and main group metals, including $NH_4^+$, n-propylammonium, Li, Na, K, Rb, Cs, Mg, Ca, Sr, Ba, La, Ce, Sm, Pr, Yb, Sc, Y, Ti, Zr, Hf, Al, Ga, In, Sn, Bi, and mixtures thereof, "b" is the mole ratio of M2 cations and metals to the M1 metals and is greater than or equal to 0, "n" is the weighted average valence of the M2 cations and metals and is greater than 0, M3 is selected from the main group elements that form complex oxoanions such as C, Si, P, and Ge, "c" is the mole ratio of M3 to the M1 metals and is greater than or equal to 0, "p" is the weighted average valence of M3 and is greater than 0, "d" is mole ratio of hydrogen to the M1 metals and varies from 0 to about "z", "z" is mole ratio of O to M1 metals and is given by $$z = (a \; m + b \cdot n + c \cdot p + d)/2$$

Any combination of these oxides can be mixed in any proportion to obtain the desired catalyst provided the weight fraction of M1 in the catalyst falls in the 0.1% to 90% range.

Another embodiment of the catalyst comprises at least one transition metal M1 selected from the group Mn, Co, Cr, V, Mo, Fe, Cu, and Ni, supported on an inorganic support selected from the group consisting essentially of at least one of the simple oxides, complex oxides, phosphates, silicates, germanates and carbonates of the alkali metals, alkaline earth metals, early transition metals such as Sc, Ti, Y, Zr, Lu, and Hf, rare earth metals, and main group metals such as Al, Ga, Si, Ge, In, and Bi, such that the M1 metals comprise a 0.1% to 90% weight fraction of the catalyst.

The present invention is applicable for the oxidation of organic compounds containing at least one carbon-hydrogen bond capable of being oxidized to a hydroperoxide-carbon bond. Organic compounds which may be oxidized in accordance with the present invention are normal alkanes, branched alkanes, normal alkenes, branched alkenes, alkylated aromatics, analogous compounds also containing heteroatoms (oxygen, nitrogen, sulfur, etc.) and mixtures of such compounds as are typically found in refinery hydrocarbon streams, for example.

Organic compounds which may be oxidized in accordance with the present inventions are polymers having suitable hydrogen-carbon bonds. Preferred polymer starting materials are those consisting essentially of carbon and hydrogen. Especially preferred polymers are polymers of conjugated dienes that have had at least a portion of their unsaturation subjected to hydrogenation. Such hydrogenated polymers of conjugated diolefins and methods for preparing them are known in the art. When polymers are oxidized in accordance with the present invention, the resulting product will be a polymeric hydroperoxide which, of course, may contain more than one hydroperoxide group per polymer molecule. Such polymeric hydroperoxides have utility as polymeric initiator species for free radical type reactions and can serve as the base polymer for graft polymerization reactions utilizing the hydroperoxide group as a reaction site in the polymer chain.

Another class of organic compound which can be used as feedstock in the present invention includes organic compounds having the formula

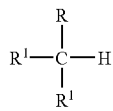

wherein R is hydrogen, an alkyl radical, or an aromatic radical, each $R^1$ is individually selected from hydrogen or hydrocarbyl alkyl radical, or the two $R^1$ groups are joined to form a saturated hydrocarbyl carbocyclic ring. The preferred compounds have from 3 to about 50 carbon atoms and more preferably from 3 to about 30 carbon atoms. Examples of such hydrocarbyl compounds include propane, 2-methyl propane, 4-methyl heptane, 6,8-dipentyleicosane, cyclopentane, cyclohexane, cyclooctane, cyclododecane, methylcyclopentane, 1,4-dimethylcyclohexane, cyclohexylbenzene, and the like.

Another preferred class of feed organic compounds of the formula

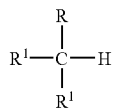

as above defined, are those aromatic compounds having 8 to 50 carbon atoms per molecule where R is an aromatic radical. The aromatic radical can include any sort of substitution that does not prevent the oxidation of the present invention. Examples of suitable substituents include halogen, nitro, alkyl, carboxyalkyl and the like. Examples of such compounds include toluene, xylenes, ethylbenzene, p-chlorotoluene, p-nitrotoluene, isopropylbenzene, cyclopentylbenzene, cyclohexylbenzene, C4–C20 linear alkylbenzene, C4–C20 branched alkylbenzene, C1–C20 alkylnaphthalenes, C1–C20 alkylanthracene, tetrahydronaphthalene, C1–C20 alkylated tetrahydronaphthalene, C1–C20 tetrahydroanthracene and the like. The most preferred of these aromatic compounds are the hydrocarbyl aromatic, that is, those containing only hydrogen and carbon.

The molecular hydroperoxides like the polymeric hydroperoxides generally have utility as initiators in free radical polymerization systems. Furthermore, generally such hydroperoxides can be treated further under acidic hydrolysis conditions to provide cleavage products such as hydroxyl compounds or carbonyl compounds. In addition such hydroperoxides generally can also be utilized as catalyst components for the epoxidation of olefinic compounds in the presence of tungsten or molybdenum or their compounds.

The catalysts which are utilized in the present invention provide an increase in the rate of oxidation in the production of hydroperoxide compounds. The catalysts include the simple and complex transition metal oxide based materials described above containing the M1 metals Mn, Co, Cr, V, Mo, Fe, Cu, and Ni, while another possibility is these same M1 species supported on an inorganic support selected from the group consisting of at least one of the simple oxides, complex oxides, phosphates, silicates, germanates and carbonates of the alkali metals, alkaline earth metals, early transition metals such as Sc, Ti, Y, Zr, Lu, and Hf, rare earth metals, and main group metals such as Al, Ga, Si, Ge, In, and Bi.

The simple and complex oxide catalysts of this invention may be derived by a wide variety of synthetic methods. Many oxide-based materials, both simple and that contain the M1 metals, Mn, Co, Cr, V, Mo, Fe, Cu, and Ni, or some combination thereof, may be purchased commercially. Synthesis methods that can yield suitable catalysts include co-precipitation, sol-gel synthesis, hydrothermal synthesis, synthesis in ionic liquids, organic solvents and other non-aqueous media, solid state methods including mixing solid components or solids and solution components that are treated at an appropriate temperature under an appropriate gaseous atmosphere (or vacuum) to bring about the desired chemistry, or any combination of these methods.

Examples of simple oxides, complex oxides, and mixtures thereof that may be obtained by these methods are MnO, $Mn_2O_3$, $MnO_2$, $KMn_8O_{16}$, $Li_2MnO_3/Li_2O/Na_3PO_4$, organoammonium vanadium phosphates, organoammonium molybdenum phosphates, $MnMoO_4$, $Mg_6MnO_8$, CoO, $Co_2O_3$, $Cr_2O_3$, $K_3Mn_4P_3O_{16}$, NiO, $Fe_2O_3$, $FePO_4$, $V_2O_5$, $MoO_3$, and CuO.

The supported catalysts of this invention can be prepared by any of the methods known in the art. For example, the supported catalysts can be prepared by dry mixing the components or by impregnating the support with a solution or dispersion of the M1 metals. In accordance with the present invention, the catalyst may contain, the metal oxide, complex metal oxides, or mixed phases wherein the metal and the support co-exist in a phase distinct from the metal oxides and the parent support.

Examples of suitable supported catalysts for the practice of this invention include manganese on magnesium oxide, manganese on aluminum oxide, manganese zirconium oxide, manganese on lithium zirconate, manganese on hydroxyapatite, cobalt on magnesium oxide, cobalt on zirconium oxide, nickel on magnesium oxide, nickel on zirconium oxide, chromium on magnesium oxide, chromium on zirconium oxide, molybdenum on magnesium oxide, molybdenum on zirconium oxide, iron on magnesium oxide and iron on zirconium oxide.

The amount of metal present on the supported catalyst can range widely but generally will be in the range from about 0.1 to about 90 weight percent and preferably from about 1 to about 25 weight percent based on the finished catalyst.

In the hydrocarbon oxidation of the present invention, the amount of supported catalyst utilized is any catalytically effective amount. Generally, this amount is in the range from about 0.001 to about 10 weight percent and preferably from about 0.01 to about 5 weight percent based on the hydrocarbon feedstock. In the case where the catalyst is employed in a fixed bed and the feedstock is passed over the catalyst, it is preferred that the liquid hourly space velocity (LHSV) is in the range from about 0.01 to about 40 hr$^{-1}$ and preferably from about 0.1 to about 25 hr$^{-1}$.

Any suitable amount of oxygen can be employed. Preferably, enough oxygen is employed to obtain maximum conversion of the organic reactant or reactants. The amount of oxygen employed can be expressed in terms of the mole ratio of oxygen to that of organic compound that is to be oxidized. Generally; this ratio is in the range from about 0.005:1 to about 20:1 or higher and preferably in the range of about 0.01:1 to about 2:1. The oxygen may be introduced into the reaction zone in any manner that will result in oxygen contacting the feedstock to be oxidized. For example, the reaction mixture can be merely stirred under an oxygen atmosphere at atmospheric pressure or above, or oxygen can be bubbled through the reaction mixture. Air, as well as other mixtures of gases with oxygen, may be utilized as the source of oxygen. The pressure utilized during the reaction may be atmospheric or superatmospheric and will generally range from about 100 kpa (0 psig) to about 7.0 MPa (1000 psig) and will preferably range from about 100 kPa (0 psig) to about 3.5 MPa (500 psig).

The temperature utilized in the present invention can vary widely and of course, as mentioned earlier, lower temperatures tend to result in higher selectivity to hydroperoxides. The reaction temperature may be in the range from about 25° C. (77° F.) to about 200° C. (392° F.), preferably from about 80° C. (176° F.) to about 180° C. (356° F.). The contact time of the reactant and the catalyst depends upon the temperature employed and the degree of conversion that is desired. At prolonged times, the yield of hydroperoxides increases, reaching a maximum, and then declines because of decomposition of the hydroperoxides. Generally, in a static reaction system, the reaction is conducted for a time in the range from about 5 minutes to 2 days.

During the reaction, it may be desirable to utilize a portion of the previous reaction mixture or product as an ingredient in the charge of a fresh feedstock since this may eliminate an induction period that might occur otherwise. In this regard, induction periods may also be essentially eliminated by the addition of a small amount of a hydroperoxide other than the hydroperoxide product expected. In this context, the hydroperoxide is called an initiator. Hydroperoxides that are suitable initiators are those which decompose under the reaction conditions quickly enough to reduce the induction periods. Examples of suitable initiators include cumene hydroperoxide and cyclohexylbenzene hydroperoxide. Generally, hydroperoxide initiators are effective in amounts in the range from about 0.5 to about 1.5 weight percent of the fresh feedstock.

The oxidation reaction in accordance with the present invention can be carried out in any batch or continuous reactor that is capable of withstanding the pressures and oxidizing conditions which are present. The reaction vessel may be lined with materials such as glass or ceramic or constructed of materials such as stainless steel, Monel, titanium, Inconel or the like. In a continuous process, the reactants may be passed through the reaction zone containing the supported catalysts and the reactor effluent then treated to remove the hydroperoxide product or sent to a further processing stage.

The X-ray patterns presented in the following examples (and tables above) were obtained using standard X-ray powder diffraction techniques. The radiation source was a high-intensity X-ray tube operated at 45 kV and 35 ma. The diffraction pattern from the copper K-alpha radiation was obtained by appropriate computer based techniques. Flat compressed powder samples were continuously scanned at 2° (2θ) per minute from 2° to 70° (2θ). Interplanar spacings (d) in Angstrom units were obtained from the position of the diffraction peaks expressed as 2θ where θ is the Bragg angle as observed from digitized data. Intensities were determined from the integrated area of diffraction peaks after subtracting background, "$I_o$" being the of the strongest line or peak, and "I" being the intensity of each of the other peaks.

As will be understood by those skilled in the art, the determination of the parameter 2θ is subject to both human and mechanical error, which in combination can impose an uncertainty of about ±0.4 on each reported value of 2θ and up to ±0.5 on reported values for nanocrystalline materials. This uncertainty is, of course, also manifested in the reported values of the d-spacing, which are calculated from the θ values. This imprecision is general throughout the art and is not sufficient to preclude the differentiation of the present crystalline materials from each other and from the compositions of the prior art. In certain instances the purity of a synthesized product may be assessed with reference to its X-ray powder diffraction pattern. Thus, for example, if a sample is stated to be pure, it is intended only that the X-ray pattern of the sample is free of lines attributable to crystalline impurities, not that there are no amorphous materials present.

The present invention is further demonstrated by the following examples. These examples are, however, not presented to unduly limit the process of this invention, but to further illustrate the advantages thereof.

EXAMPLE 1

In a typical preparation, an aqueous solution was prepared by dissolving 31.71 g manganese acetate tetrahydrate, $Mn(OAc)_2 \cdot 4H_2O$ in 301.2 g deionized water. Powdered MgO (20.2 g) was added to this solution, stirred vigorously for 1 hour and transferred to a steam-jacketed glass rotary evaporating vessel. This reaction mixture was evaporated to dryness over 3–4 hours. The resulting solid was calcined under flowing air while ramping from room temperature to 600° C. at a rate of 2° C./min, dwelling at 600° C. for 4 hours, and cooling back to room temperature. Bulk chemical analysis gave 34.7 wt % Mg, 25.2 wt % Mn, and 2.74 wt % volatiles, corresponding to the mole ratio Mg/Mn=3.14. Characterization by X-Ray powder diffraction indicated the material had the structure of the complex oxide $MnMg_6O_8$. Characteristic diffraction lines observed for the product are given in Table 1.

TABLE 1

| 2-Θ | d (Å) | I/Io % |
|---|---|---|
| 18.34 | 4.83 | 34 |
| 35.72 | 2.51 | 34 |
| 37.12 | 2.42 | 13 |
| 43.18 | 2.09 | 100 |
| 57.08 | 1.61 | 5.5 |
| 62.82 | 1.48 | 51 |
| 65.86 | 1.42 | 1.7 |

One hundred grams of a hydrotreated diesel having the characteristics presented in Table 2 was charged to a stirred autoclave in addition to four grams of the hereinabove described catalyst. The autoclave was pressured to 7.7 MPa (1100 psig) with a gas mixture containing 8 volume percent oxygen and 92% volume percent nitrogen and then heated to 125° C. (257° F.) for one hour. After cooling and venting the autoclave to atmospheric pressure, the liquid hydrocarbon product was analyzed and to contain 0.96 weight percent peroxide expressed as hydrogen peroxide weight percent equivalent.

TABLE 2

Hydrotreated Diesel

| Initial Boiling Point, ° C. | 209 |
|---|---|
| End Boiling Point, ° C. | 326 |
| Specific Gravity | 0.8586 |
| Sulfur, wppm | 386 |
| Nitrogen, wppm | 18 |
| 1 Ring Aromatics, volume percent | 30.2 |
| 2 Ring Aromatics, volume percent | 5.5 |
| Polyaromatics, volume percent | 0.6 |
| Peroxides, weight percent | 0.0038 |

Comparative Example 1

Example 1 was repeated using the same feed and reaction conditions but in the absence of catalyst and the final product was found to contain 0.018 weight percent peroxides.

EXAMPLE 2

A solution was prepared by dissolving 4.14 g $LiNO_3$ in 20.6 g deionized water. To this solution, 0.71 g $Mn(OAc)_2 \cdot 4H_2O$ were added while stirring. To the resultant clear solution, $Li_2ZrO_3$ (15.42 g) was added with vigorous stirring that was continued for 0.5 hour. The reaction mixture was then transferred to a steam-jacketed rotary evaporator vessel and evaporated to dryness over 3–4 hours. The dry solids, 17.7 g, were then pressed into a 1 inch circular pellet under 138 MPa (20,000 psi). The resultant pellet was calcined in flowing air in according to the following program: ramp at 2 from room temperature to 100° C., dwell at 100° C. for 2 hours, ramp at 2° C./min from 100 to 350° C., dwell at 350° C. for 2 hours, ramp at 5° C./min from 350 to 800° C., and dwell at 800° C. for 6 hours before cooling to room temperature. The pellet was crushed and analyzed by bulk chemical analysis to give 9.14 wt % Li, 1.04 wt % Mn, 53.5 wt % Zr with 4.07 wt % volatiles, yielding the mole ratios Li/Zr=2.24 and Mn/Zr=0.032. Characterization by x-ray powder diffraction showed the product to consist predominantly of a mixture of complex and simple oxides, including the support, $Li_2ZrO_3$, zirconia (baddeleyite), and $Li_2MnO_3$. Characteristic lines for this catalyst is given in Table 3.

TABLE 3

| 2-Θ | d (Å) | I/Io % |
|---|---|---|
| 18.60 | 4.77 | 10 |
| 19.54 | 4.54 | 17 |
| 20.16 | 4.40 | 100 |
| 21.88 | 4.06 | 41 |
| 23.99 | 3.71 | 2 |
| 24.40 | 3.64 | 1 |
| 26.48 | 3.36 | 60 |
| 28.10 | 3.17 | 18 |
| 31.28 | 2.86 | 24 |
| 34.00 | 2.63 | 6 |
| 34.68 | 2.58 | 24 |
| 35.24 | 2.54 | 4 |
| 35.74 | 2.51 | 28 |
| 36.88 | 2.44 | 3 |
| 38.82 | 2.32 | 16 |
| 39.80 | 2.26 | 46 |
| 40.54 | 2.22 | 3 |

TABLE 3-continued

| 2-Θ | d (Å) | I/Io % |
|---|---|---|
| 41.12 | 2.19 | 9 |
| 42.38 | 2.13 | 67 |
| 43.88 | 2.06 | 10 |
| 44.64 | 2.03 | 19 |
| 45.47 | 1.99 | 1 |
| 47.44 | 1.91 | 10 |
| 48.91 | 1.86 | 2 |
| 49.16 | 1.85 | 3 |
| 50.10 | 1.82 | 5 |
| 50.74 | 1.80 | 16 |
| 51.52 | 1.77 | 4 |
| 52.80 | 1.73 | 4 |
| 53.84 | 1.70 | 19 |
| 54.66 | 1.68 | 11 |
| 55.32 | 1.66 | 1 |
| 55.92 | 1.64 | 4 |
| 56.88 | 1.62 | 8 |
| 57.62 | 1.60 | 1 |
| 58.94 | 1.57 | 6 |
| 59.60 | 1.55 | 46 |
| 61.60 | 1.50 | 27 |
| 62.44 | 1.49 | 2 |
| 62.76 | 1.48 | 4 |
| 64.52 | 1.44 | 2 |
| 65.40 | 1.43 | 4 |
| 66.24 | 1.41 | 3 |
| 68.22 | 1.37 | 3 |
| 68.84 | 1.36 | 1 |

One hundred grams of a hydrotreated light cycle oil having the characteristics presented in Table 4 was charged to a stirred autoclave in addition to four grams of the hereinabove described catalyst. The autoclave was pressured to 7.7 MPa (1100 psig) with a gas mixture containing 8 volume percent oxygen and 92 volume percent nitrogen and then heated to 125° C. (257° F.) for one hour. After cooling and venting the autoclave to atmospheric pressure, the liquid hydrocarbon product was analyzed and found to contain 2.2 weight percent peroxide expressed as hydrogen peroxide weight percent equivalent.

TABLE 4

Light Cycle Oil

| Initial Boiling Point, ° C. | 164 |
|---|---|
| End Boiling Point, ° C. | 348 |
| Specific Gravity | 0.92 |
| Sulfur, wppm | 34 |
| Nitrogen, wppm | 5 |
| 1 Ring Aromatics, volume percent | 57 |
| 2 Ring Aromatics, volume percent | 9 |
| Polyaromatics, volume percent | 1 |
| Peroxides, weight percent | — |

Comparative Example 2

Example 2 was repeated in the absence of catalyst and the liquid hydrocarbon product was found to only contain 35 wppm of peroxide equivalent.

EXAMPLE 3

An alumina-supported Mn catalyst was prepared as follows. Gamma alumina spheres of moderate bulk density (0.45–0.6 g/cc), 26.4 g, was added to a manganese acetate solution (3.7 g $Mn(OAc)_2 \cdot 4H_2O$ dissolved in 100.0 g deionized water). This mixture was stirred vigorously for 0.5 hour then transferred to a steam-jacketed glass rotary evaporating vessel. The mixture was then evaporated to dryness over 2–3 hour period. The dry solids were then calcined in flowing air, ramping to 600° C. at a rate of 2° C./min, followed by a 4 hour dwell at 600° C. Powder x-ray diffraction on a crushed sample of the catalyst showed only the presence of the alumina phase.

Sixty three grams of a hydrotreated diesel having the characteristics presented in Table 2 was charged to a stirred autoclave in addition to 2.4 grams of the hereinabove described catalyst. The autoclave was pressured to 3.9 MPa (550 psig) with a gas mixture containing 8 volume percent oxygen and 92% volume percent nitrogen and then heated to 125° C. (257° F.) for one hour. After cooling and venting the to atmospheric pressure, the liquid hydrocarbon product was analyzed and found to contain 0.19 weight percent peroxide expressed as hydrogen peroxide weight percent equivalent.

EXAMPLE 4 ($Mn^{2+}O$)

A crystalline sample of the simple oxide MnO was evaluated for the preparation of hydroperoxides by oxidizing hydrocarbon compounds in the presence of an oxygen containing gas. Seventy five grams of a hydrotreated diesel having the characteristics presented in Table 2 was charged to a stirred autoclave in addition to 3.00 grams of the hereinabove described catalyst. The autoclave was pressured to 3.9 MPa (550 psig) with a gas mixture containing 8 volume percent oxygen and 92% volume percent nitrogen and then heated to 125° C. (257° F.) for one hour. After cooling and venting the autoclave to atmospheric pressure, the liquid hydrocarbon product was analyzed and found to contain 0.26 weight percent peroxide expressed as hydrogen peroxide weight percent equivalent.

EXAMPLE 5

A sodium manganese phosphate solution with molar composition 2.5 Na: 10 P: 1 Mn was prepared according to Example 1 of U.S. Pat. No. 5,780,003, which is hereby incorporated by reference. A freshly filtered 750.5 g portion of this solution was added to a 1 liter Teflon® bottle, followed by the dropwise addition of NaOH solution (52.74 g NaOH (97%) dissolved in 159.22 g deionized water) while stirring rapidly. The resultant mixture was stirred vigorously for 0.5 hours. The homogenized mixture was divided into two portions and digested in Teflon bottles overnight at 100° C. The solid products were isolated by vacuum filtration, washed with deionized water and dried in ambient air. The dried solids were then suspended in a Li nitrate solution (28.33 g $LiNO_3$ dissolved in 75.0 g deionized water) with vigorous stirring. The slurry was then transferred to a steam-jacketed glass rotary evaporating vessel, cold rolled briefly before evaporating to dryness. The resultant solids were pelletized and calcined in Ni crucibles under flowing air, ramping at 5° C./min to 900° C. followed by a 6 hr dwell. Bulk elemental analysis of the calcined material gave 14.6 wt. % Li, 31.0 wt. % Mn, 4.10 wt. % P and 6.94 wt. % Na, yielding the molar ratios Li/Mn=3.72, P/Mn=0.23, Na/Mn=0.53. Characteristic lines in the x-ray diffraction pattern showed the catalyst to consist predominantly of $Li_2MnO_3$ and $Li_2O$, and minor amounts of unidentified phases. Representative diffraction lines for this catalyst are shown in Table 7.

TABLE 7

| 2-Θ | d (Å) | I/Io % |
|---|---|---|
| 18.64 | 4.76 | 98 |
| 20.77 | 4.27 | 16 |
| 21.68 | 4.10 | 11 |
| 21.92 | 4.05 | 11 |
| 24.14 | 3.68 | 1 |
| 25.27 | 3.52 | 3 |
| 25.85 | 3.44 | 2 |
| 28.07 | 3.18 | 1 |
| 31.44 | 2.84 | 1 |
| 32.48 | 2.75 | 2 |
| 32.88 | 2.72 | 2 |
| 33.56 | 2.67 | 15 |
| 35.86 | 2.50 | 3 |
| 36.34 | 2.47 | 4 |
| 36.94 | 2.43 | 33 |
| 37.88 | 2.37 | 1 |
| 38.56 | 2.33 | 3 |
| 38.94 | 2.31 | 1 |
| 44.64 | 2.03 | 100 |
| 48.82 | 1.86 | 9 |
| 56.32 | 1.63 | 8 |
| 58.82 | 1.57 | 14 |
| 61.74 | 1.50 | 1 |
| 64.52 | 1.44 | 22 |
| 65.52 | 1.42 | 22 |
| 66.77 | 1.40 | 1 |
| 67.23 | 1.39 | 3 |
| 68.82 | 1.36 | 12 |

Twenty grams of a hydrotreated diesel having the characteristics presented in Table 2 was charged to a stirred autoclave in addition to 0.3 grams of the hereinabove described catalyst. The autoclave was pressured to 7.7 MPa (1100 psig) with a gas mixture containing 8 volume percent oxygen and 92% volume percent nitrogen and then heated to 125° C. (257° F.) for one hour. After cooling and venting the autoclave to atmospheric pressure, the liquid hydrocarbon product was analyzed and to contain 0.37 weight percent peroxide expressed as hydrogen peroxide weight percent equivalent.

The foregoing description and examples clearly illustrate the advantages encompassed by the catalyst and process of the present invention and the benefits to be afforded therefrom.

What is claimed is:

1. A process for producing an organic hydroperoxide comprising reacting an organic compound having at least one carbon-hydrogen bond capable of being oxidized to a hydroperoxide-carbon bond with oxygen in the presence of a catalyst comprising a transition metal oxides of empirical formulation in the anhydrous state $$(M1)_a^{m+}H_dO_z$$

where M1 is a transition metal selected from the set Mn, Co, Cr, V, Mo, Fe, Cu, and Ni, which comprises between 0.1% and 90% of the catalyst by weight, "a" is the moles of the M1 metal in the transition metal oxide and is defined to be equal to 1, "m" is the average valence of M1 and is greater than 0, "d" is the mole ratio of hydrogen to M1 and varies from 0 to about "z", and "z" is the mole ratio of O to M1 and is given by $$z=(a \cdot m+d)/2=(m+d)/2.$$

2. The process of claim 1 wherein the organic compound is selected from the group consisting essentially of hydrocarbonaceous compounds having from about 5 to about 30 carbon atoms.

3. The process of claim 1 wherein the organic compound is an aryl alkyl hydrocarbon.

4. The process of claim 1 wherein the organic compound is a heterocyclic compound.

5. The process of claim 1 wherein the organic compound is a heterocyclic compound containing sulfur.

6. The process of claim 1 wherein reaction conditions include a temperature from about 43° C. (110° F.) to about 260° C. (500° F.) and a pressure from about 100 kPa (0 psig) to about 3.5 MPa (500 psig).

7. A process for producing an organic hydroperoxide comprising reacting an organic compound having at least one carbon-hydrogen bond capable of being oxidized to a hydroperoxide-carbon bond with oxygen in the presence of a catalyst comprising physical mixtures of transition metal oxides, the mixture given by the empirical formula when in the anhydrous state $$(M1)_a^{m+}H_dO_z$$

where M1 includes at least two metals selected from the group Mn, Co, Cr, V, Mo, Fe, Cu, and Ni, which together comprise between 0.1% and 90% of the catalyst by weight, "a" is the sum of the mole fractions of the individual M1 metals and is defined to be 1, "m" is the weighted average valence of the M1 metals and is greater than 0, "d" is the mole ratio of hydrogen to the moles of M1 metals and varies from 0 to about "z", and z is the mole ratio of oxygen to the M1 metals and is given by $$z=(a \cdot m+d)/2.$$

8. The process of claim 7 wherein the organic compound is selected from the group consisting essentially of hydrocarbonaceous compounds having from about 5 to about 30 carbon atoms.

9. The process of claim 7 wherein the organic compound is an aryl alkyl hydrocarbon.

10. The process of claim 7 wherein the organic compound is a heterocyclic compound.

11. The process of claim 7 wherein the organic compound is a heterocyclic compound containing sulfur.

12. The process of claim 7 wherein reaction conditions include a temperature from about 43° C. (110° F.) to about 260° C. (500° F.) and a pressure from about 100 kPa (0 psig) to about 3.5 MPa (500 psig).

* * * * *